United States Patent [19]

Tashiro

[11] Patent Number: 4,790,295

[45] Date of Patent: Dec. 13, 1988

[54] ENDOSCOPE HAVING TRANSPARENT RESIN SEALING LAYER

[75] Inventor: Yoshio Tashiro, Tokyo, Japan

[73] Assignee: Olympus Optical Co., Ltd., Tokyo, Japan

[21] Appl. No.: 130,090

[22] Filed: Dec. 8, 1987

[30] Foreign Application Priority Data

Dec. 16, 1986 [JP] Japan .................................. 61-297728
Mar. 20, 1987 [JP] Japan .................................. 62-67241

[51] Int. Cl.$^4$ ................................................. A61B 1/06
[52] U.S. Cl. ........................................................ 128/6
[58] Field of Search ............................. 128/3, 4, 5, 6, 7

[56] References Cited

U.S. PATENT DOCUMENTS 4,273,109  6/1981  Enderby ............................... 128/6
4,350,150  9/1982  Kubota et al. ........................ 128/6
4,576,146  3/1986  Kawazoe et al. ..................... 128/6
4,587,972  5/1986  Morantte, Jr. ..................... 128/4 X

FOREIGN PATENT DOCUMENTS 61-20371  7/1986  Japan .
61-14312  9/1986  Japan .
62-84012  5/1987  Japan .

Primary Examiner—William H. Grieb
Attorney, Agent, or Firm—Ladas & Parry

[57] ABSTRACT

The endoscope of the invention has a very fine insertion section which is capable of being inserted into, for example, a blood vessel. The insertion section has at its outer periphery a thin-walled hollow cylindrical sheath, one end of which has an opening to the outside. The sheath contains a light guide fiber bundle for emitting a beam of illumination light into the blood vessel, an object lens group for receiving a beam reflected from the blood vessel, in order to form an image, and an image guide fiber bundle for transmitting the image formed. In addition, the sheath has at one end thereof a recess portion having a side wall defined by the sheath, a bottom wall defined by the light guide fiber bundle, and an opening to the outside. A transparent resin layer of a uniform thickness is arranged within the recess portion, and seals the inside of the sheath at one end, one end face of the resin layer being substantially flush with the one end of the sheath.

11 Claims, 4 Drawing Sheets

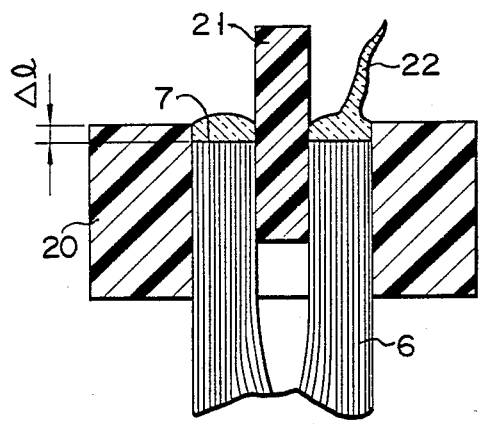
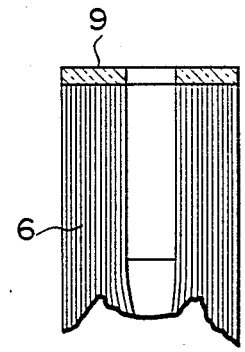
FIG. 9　　　　　FIG. 10
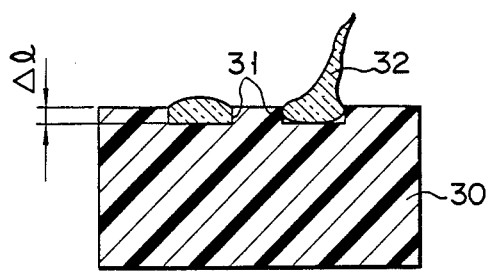
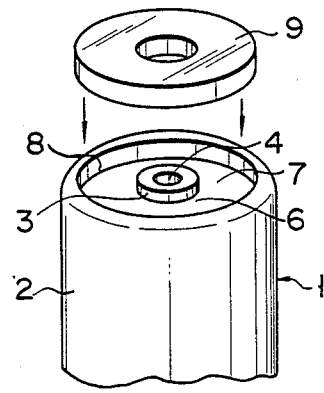
FIG. 11　　　　　FIG. 12

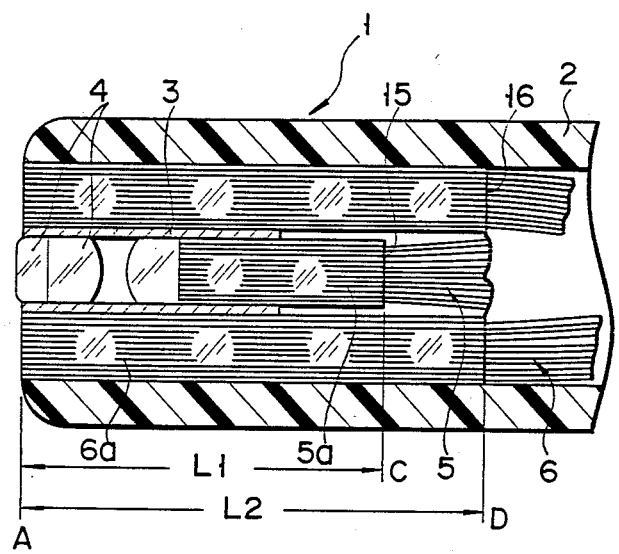
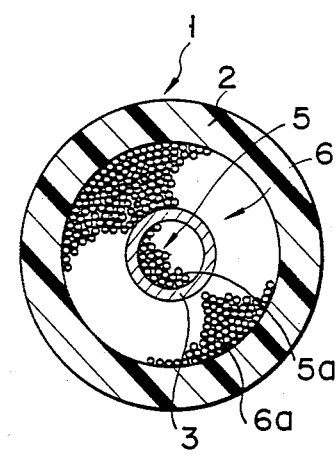
FIG. 13  FIG. 14
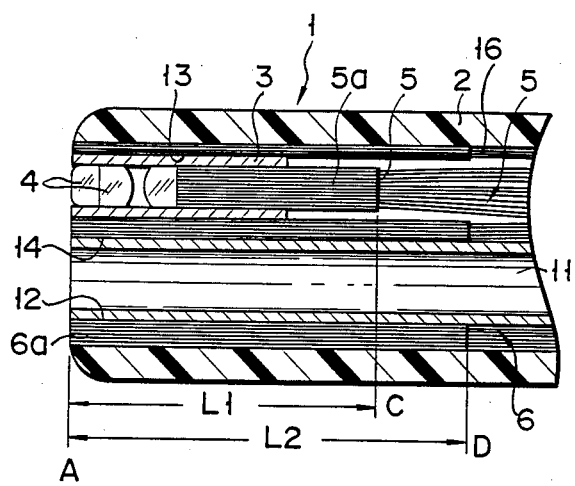
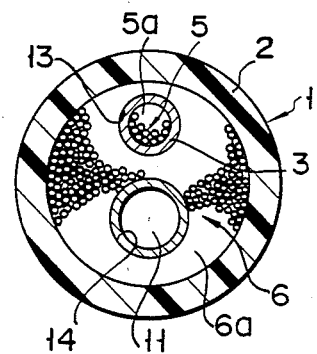
FIG. 15  FIG. 16

ENDOSCOPE HAVING TRANSPARENT RESIN SEALING LAYER

BACKGROUND OF THE INVENTION

The present invention relates to an endoscope having a very fine insertion section, which is able to enter, for example, a blood vessel.

A conventional endoscope comprises an insertion section which can be inserted into a body cavity, and a control section for controlling the insertion section from outside of the body cavity. The distal end of the insertion section has an illumination window incorporated therein, for illuminating the body cavity, as well as an observation window for receiving a light beam which is irradiated from the illumination window and reflected by the wall of the body cavity. Arranged within insertion section are a light guide fiber bundle for transmitting an illumination light beam emitted from an external light source, an illumination lens for diffusing the light beam transmitted through the light guide fiber bundle, an object lens for forming an image of the interior of the body cavity, based on the beam incident through the illumination window, and an image guide fiber bundle for transmitting the image formed by the object lens to outside of the body cavity. The light-emission end portion of the light guide fiber bundle is cylindrical in shape, as is the illumination lens, which faces the light-emission end portion.

The outer diameter of an endoscope insertion section able to enter a blood vessel must, as a matter of course, be very small. Therefore, if the light-emission end portion of the light guide fiber bundle is cylindrical in shape, this results in a decrease in the cross section of the end portion, with a consequent decrease in the amount of illumination light which can be transmitted therethrough.

An endoscope is known, the light-emission end of the light guide fiber bundle of which is formed as a hollow cylinder, in order to surround the object lens. In this way, the cross section of the light-emission end portion can be increased, increasing the amount of light which can be transmitted therethrough, while the outer diameter of the insertion section can be kept small. In the case of this endoscope, it is necessary that the shape of the illumination lens correspond to the shape of the light-emission end of the light guide fiber bundle. However, the formation of a hollow cylindrical illumination lens is technically difficult, inevitably resulting in high manufacturing costs.

An endoscope having a very fine insertion section is used mainly to observe narrow, confined areas such as the interior of blood vessels. In such restricted areas, the lens effect, for diffusing illumination light, is not required. Accordingly, an endoscope is known, the end face of the light guide fiber bundle of which is exposed. Having no illumination lens, such an endoscope is relatively simple in structure and can thus be manufactured at low cost.

However, this type of endoscope does have the following drawbacks:

With increasing number of patients receiving medical treatment involving the use of an endoscope, it has become ever more important to ensure that the device be thoroughly sterilized each time use is made thereof. This results in the endoscope being frequently immersed in sterilizer liquid. Over time, however, coloring and erosive substances contained in the sterilizer liquid damage the light-emisssion end face of the light guide fiber bundle, reducing the amount of light which can be emitted therefrom.

Japanese Utility Model Disclosure (Kokai) No. 61-143120/86 proposes an endoscope wherein, for example, an epoxy resin ahhesive is coated on the light-emission end face of the light guide fiber bundle, in order to protect the exposed end face thereof against the harmful effects of sterilizer liquid. In Disclosure No. 61-143120/86, the object lens projects from the end face of the light-emission end portion of the light guide fiber bundle. A stepped portion is formed between the object lens and the light guide fiber bundle, and is filled with resin, the outer face of the body of resin formed therein being made convex.

Since the resin layer used in the endoscope of Disclosure No. 61-143120/86 is of convex lens shape, this results in the resin layer being disadvantageously thick. While a number of epoxy resins and acryl resins possess a relatively high transparency, when formed as a layer, the thicker the layer is formed, the lower the degree of transparency becomes, with a consequent lowering of the light transmittance thereof. Compared to normal endoscopes, an endoscope having a very fine insertion section contains a lower number of light guide fibers. Therefore, any loss in the light transmittance of the light guide fibers of this type of endoscope represents a much more serious operating disadvantage than in the case of the conventional device.

Furthermore, epoxy, acryl, silicone resins have fluidity until they completely harden. Distortion may likely occur in a convex-lens-shaped layer made of such resins. Also, since the resin layer is exposed, the surface of the resin layer may likely be damaged by outside solid articles. If the surface of the resin layer is scarred, the light transmission degree is lowered. In the worst case, the resin layer may be detached from the endoscope.

The object of the present invention is to provide an endoscope which can overcome the problems in prior art, wherein a transparent resin layer of a uniform thickness can be formed easily and economically on an end face of a light guide fiber bundle. The resin layer has a stable strength, and is hardly damaged and detached from the endoscope.

In order to achieve the above object, the present invention provides an endoscope which comprises a small-diameter insertion section able to enter a body cavity, the insertion section having a hollow cylindrical member one end of which has an opening to the outside, said cylindrical member containing a light guide fiber bundle for emitting a beam illumination light into the body cavity, an object optical system for receiving a beam reflected from the body cavity to form an image formed, and image transmission means for transmitting the image; a recess portion having a side wall defined by said cylindrical member, a bottom wall defined by said light guide fiber bundle, and an opening at said one end of the cylindrical member; and a transparent resin layer of a uniform thickness, arranged within said recess portion and sealing the inside of said cylindrical member at said one end of the cylindrical member, said resin layer having an end face which is substantially flush with said one end of the cylindrical member.

In the present invention, one end of the sheath of the insertion section is sealed by the transparent resin layer, so that the members within the sheath are protected. Since the transparent resin layer is arranged in substantially the same plane as one end of the sheath, the resin layer can be formed easily with no special skills required. The formed resin layer is hardly damaged by external objects, and has a stable strength.

BRIEF DESCRIPTION OF THE DRAWINGS

FIG. 9 is a schematic view showing a first modification of the method of forming the resin layer in the first embodiment;

FIG. 10 is a schematic view showing the resin layer formed by the method of FIG. 9, along with a portion of the light guide fiber bundle;

FIG. 11 is a schematic view showing a second modification of the method of forming the resin layer in the first embodiment;

FIG. 12 is a schematic view showing the state in which the resin layer formed by the method of the second modification is mounted at an end portion of the insertion section;

FIG. 13 is a schematic longitudinal cross section of a part of an insertion section of an endoscope according to an example relating to the present invention;

FIG. 14 is a transverse cross section of the insertion section of the endoscope shown in FIG. 13;

FIG. 15 is a schematic longitudinal cross section of a part of an insertion section of an endoscope according to another example relating to the present invention; and FIG. 16 is a transverse cross section of the insertion section of the endoscope shown in FIG. 15.

DESCRIPTION OF THE PREFERRED EMBODIMENTS

Figure 1:
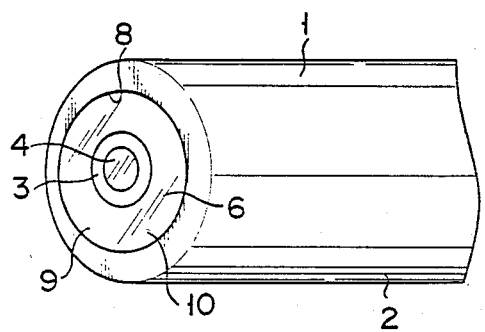
FIG. 1 is a schematic perspective view showing a part of an insertion section of an endoscope according to a first embodiment of the present invention.
Figure 2:
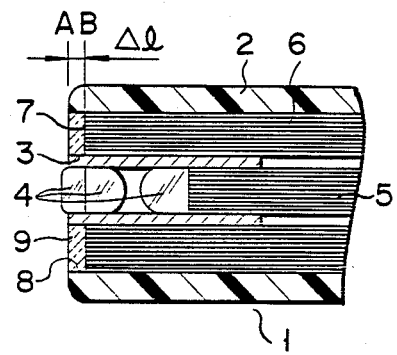
FIG. 2 is a schematic cross section of the insertion section shown in FIG. 1.
Figure 3:
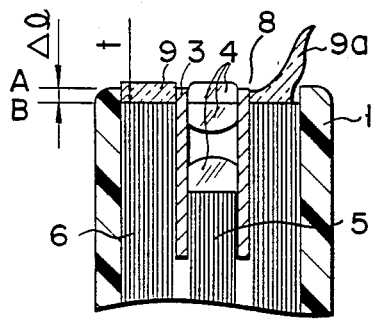
FIG. 3 is a schematic cross section of the insertion section, illustrating the state in which a resin layer is being formed in the insertion section of the endoscope of the first embodiment.

FIGS. 1, 2 and 3 show a part of the endoscope according to the first embodiment of the present invention.

In this embodiment, the endoscope has very thin insertion section 1, which can be inserted into a narrow body cavity such as a blood vessel. Insertion section 1 is connected to a control section (not shown).

The outer periphery of insertion section 1 is formed of hollow cylindrical thin sheath or cylindrical member 2. An outer edge portion of an insertion end portion or a distal end portion (the left side of FIG. 1) of sheath 2 is smoothly curved, so that the insertion end portion may be easily inserted into the body cavity. On the distal-end-side of insertion section 1, hollow cylindrical lens frame 3 is concentrically arranged within sheath 2. Axially inner and outer end portions of lens frame 3 are opened. The axially outer end portion of lens frame 3 is substantially flush with plane A which includes the end face of sheath 2. Lens frame 3 surrounds object lens group 4 which receives light beams incident from outside to form an image. The outer surface of the outermost lens of lens group 4 is substantially flush with, or slightly projects from, plane A. An end portion of image guide fiber bundle 5, which transmits an image formed by lens group 4 to the control section (not shown), is fitted in lens frame 3 behind the rear end of lens group 4. Object lens group 4 forms an image on the adjacent end face of fiber bundle 5.

Light guide fiber bundle 6 for guiding illumination light from a light source (not shown) is provided within a space defined by the inner periphery of sheath 2 and the outer periphery of lens frame 3. Fiber bundle 6 is formed of a number of closely gathered glass fibers.

End face 7 of light guide fiber bundle 6 is arranged in a plane normal to the axis of insertion section 1. End face 7 of fiber bundle 6 has an annular shape, when viewed from outside in the axial direction. Also, end face 7 is flush with plane B which is rearward of plane A by $\Delta 1$. Thus, annular groove or annular recess portion 8, which is open to the outside, is formed at the end portion of insertion section 1. Groove 8 has the outer wall defined by the inner periphery of sheath 2, the inner wall defined by the outer periphery of lens frame 3, and the bottom wall defined by end face 7 of light guide fiber bundle 6. Groove 8 is filled with transparent resin 9a such as epoxy adhesive (e.g., tradename "STY-CAST 1266"). Resin 9a is filled and hardened, thereby forming transparent resin layer 9 having end face 10 flush with plane A.

Illumination light supplied from the light source through light guide fiber bundle 6 is transmitted through transparent resin layer 9 and emitted from insertion section 2 in the axial direction.

A method of forming transparent resin layer 9 may now be described.

Object lens group 4 and image guide fiber bundle 5 are fixed in a predetermined position within lens frame 3 by using an adhesive. Light guide fiber bundle 6 is formed in a hollow cylindrical shape. Lens frame 3 is inserted into a central space defined by the inner periphery of the end portion of fiber bundle 6. The end face of lens frame 3 is projected from end face 7 of fiber bundle 6 by $\Delta 1$. The combination of lens frame 3 and light guide fiber bundle 6 is inserted into sheath 2, and is fixed therein in such a position that the end face of lens frame 3 is substantially flush with plane A of sheath 2. Thus, annular groove 8, which is open at one axial end and is defined by sheath 2, lens frame 3 and end face 7 of light guide fiber bundle 6, is formed.

As shown in FIG. 3, for example, fluidal epoxy resin adhesive 9a is filled in groove 8, so that no space remains in groove 8 and the thickness t of the resin material is $\Delta 1$. Resin 9a is hardened to obtain resin layer 9 of a uniform thickness.

Accordingly, with no special skill, one can easily form resin layer 9 having a uniform, minimum necessary thickness. In contrast, non-uniformity appears in thickness of respective resin layers produced in a conventional method wherein resin is coated on the end face of a light guide fiber bundle. When this conventional method is employed, special skill is required to provide each endoscope with a uniform light transmission degree.

In the embodiment of FIGS. 1–3, each product can be easily provided with resin layer 9 of a uniform thickness, simply by filling groove 8 of depth Δ1 with resin 9a. By changing the depth Δ1 of groove 8, resin layer 9 of an optimum thickness can be formed. Since resin layer 9 does not project from plane A, it can be protected against scars and shock.

Figure 4:
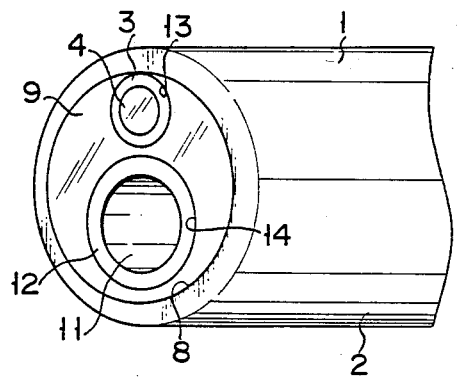
FIG. 4 is a schematic perspective view showing, like FIG. 1, a part of an insertion section of an endoscope according to a second embodiment of the present invention.
Figure 5:
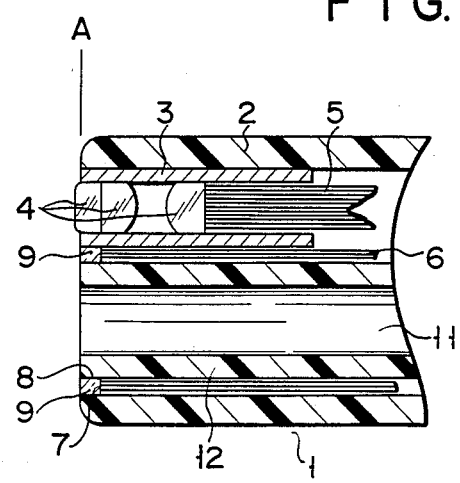
FIG. 5 is a schematic cross section of the insertion section shown in FIG. 4.

The second embodiment shown in FIGS. 4 and 5 will now be described. In FIGS. 4 and 5, the numerals already appearing in FIGS. 1–3 indicate the same elements. The description of such elements may be omitted.

In the second embodiment, the endoscope has very thin insertion section 1 for observation of the inside of a blood vessel. Within insertion section 1, axially extending channel 11 is provided.

Light guide fiber bundle 6 is arranged within sheath 2, with axially extending cylindrical spaces 13 and 14 being formed. Space 13 contains lens frame 3, and space 14 contains hollow cylindrical tube 12 which defines forceps channel 11. Therefore, small space 13 and large space 14 appear in a transverse cross section of fiber bundle 6. End faces of tube 12 and lens frame 3 are substantially flush with end face A of sheath 2. Recess portion 8 is formed at the end portion (the left side of FIG. 4) of insertion section 1. The outer peripheral wall of recess portion 8 is defined by the inner periphery of sheath 2, and the bottom wall of recess portion 8 is defined by end face 7 of light guide fiber bundle 6. Lens frame 8 and tube 12 project from the bottom wall of recess portion 8. As in the first embodiment, transparent resin layer 9 is formed within recess portion 8. Since an end face of tube 12 is substantially flush with end face A of sheath 2, and end face 7 of light guide fiber bundle 6 is retreated from end face A of sheath 2, fluidal resin filled in recess portion 8 does not enter tube 12.

Figure 6:
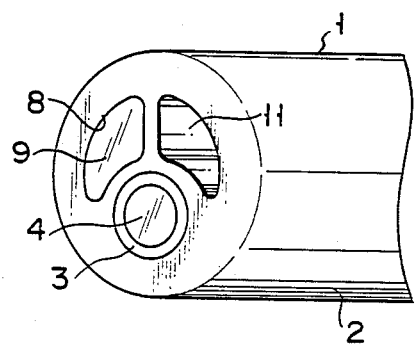
FIG. 6 is a schematic perspective view showing a part of an insertion section of an endoscope according to a third embodiment of the present invention.
Figure 7:
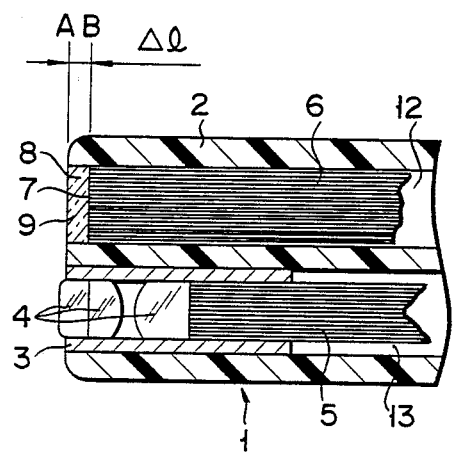
FIG. 7 is a schematic cross section of the insertion section shown in FIG. 6.

In the third embodiment shown in FIGS. 6 and 7, insertion section 1 is formed of a multi-lumen tube having a plurality of non-circular cross sectional spaces. In FIGS. 6 and 7, the previously mentioned numerals indicate the same elements, and the description of these elements may be omitted.

Cylindrical member 2 is an integral tube made of resin, and it has non-circular cross sectional spaces 11 and 12 and substantially circular cross sectional space 13. Space 11 serves as a channel. Space 13 contains, as in the first embodiment, lens frame 3, object lens group 4, and image guide fiber bundle 5. Space 12 contains light guide fiber bundle 6. Space 12 has at its end portion recess portion 8 having its peripheral wall defined by the inner wall of space 12 and its bottom wall defined by end face 7 of light guide fiber bundle 6. Transparent resin layer 9 is formed in recess portion 8, in the same method as in the first embodiment.

Figure 8:
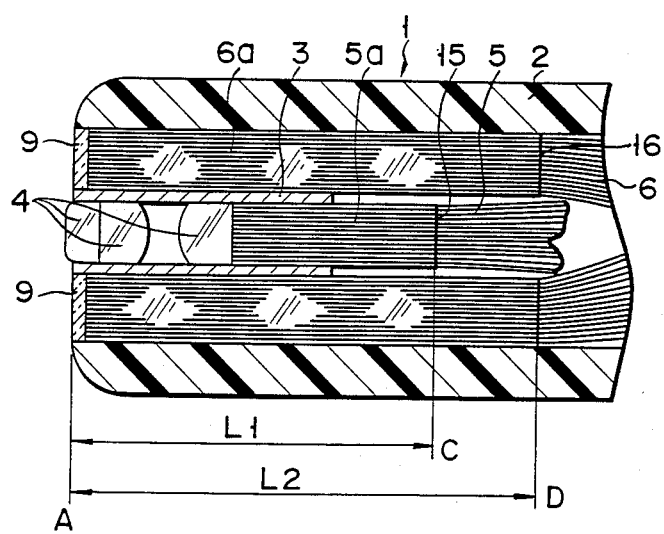
FIG. 8 is a schematic cross section of the insertion section of an endoscope according to a fourth embodiment of the present invention.

FIG. 8 shows endoscope 1 according to the fourth embodiment, wherein the image guide fiber bundle is protected against damages. Endoscope 1 is formed, in a similar method to that of the first embodiment. Image guide fiber bundle 5 has hard cylindrical portion 5a formed by bonding a number of optical fibers by an adhesive or synthetic resin. At least an end portion of hard portion 5a is inserted into lens frame 3 to adjoin object optical system 4. An rear end portion of hard portion 5a is located outside the lens frame 3. The length of hard portion 5a is determined such that, when image guide fiber bundle 5 and lens frame 3 are assembled within sheath 2, distance L1 is kept between plane A and plane C normal to the axis of sheath 2 which includes the end face of hard portion 5a.

Light guide fiber bundle 6 has also hard portion 6a. The length of hard portion 6a is determined such that, when light guide fiber bundle 6 and resin layer 9 are assembled within sheath 2, distance L2 is kept between plane A and plane D normal to the axis of sheath 2 which includes the end face of hard portion 6a.

The relationship between L1 and L2 is L1≦L2.

In the fourth embodiment, hard portion 5a of image guide fiber bundle 5 is surrounded by hard portion 6a of light guide fiber bundle 6. Thus, when bending moment is applied to the end portion of sheath 2, most of the bending moment is absorbed by sheath 2 and hard portion 6a of light guide fiber bundle 6, so that image guide fiber bundle 5 is protected against damage.

FIGS. 9 and 10 show a modification of the method of forming the resin layer. In this modification, a resin layer is formed on end face 7 of fiber bundle 6 in advance, and the fiber bundle 7 with the resin layer is inserted into the sheath.

When the endoscope of the first embodiment (FIGS. 1 and 2) is formed by using the modification of FIGS. 9 and 10, a cylindrical space for containing lens frame 3 is formed at the end of light guide fiber bundle 6. The outer diameter of fiber bundle 6 is set so that fiber bundle 6 may be fitted in sheath 2. Then, fiber bundle 6 is inserted into a hole in mold 20. The hole has the same inner diameter as sheath 2, and mold 20 is made of, for example, polytetrafluoroethylene (PTFE). End face 7 of fiber bundle 6 is retreated from the end face of mold 20 (top face of mold 20 in FIG. 9) by Δ1. Core mold 21, which is also made of PTFE and has the same diameter as lens frame 3, is inserted into the cylindrical space formed at the end portion of fiber bundle 6.

As shown in FIG. 9, resin 22 (as mentioned above) is filled in an annular groove defined by mold 20, light guide fiber bundle 6 and core mold 21. Resin 22 is filled in the annular groove up to the same level as, or a little higher level than, the end face of mold 20. After resin 22 is hardened, core mold 21 is removed. The end face of mold 20 and the end face (top face in FIG. 9) of hardened resin 22 are polished so that they are made flush with one another. Then, fiber bundle 6 is drawn out of mold 20. Thus, as shown in FIG. 10, light guide fiber bundle 6, which has resin layer 9 of a uniform thickness at its end portion (upper portion in FIG. 10) can be obtained.

As in the first embodiment, the image guide fiber bundle having the object lens group, the lens frame, and the sheath are assembled. The end faces of lens frame 3 and sheath 2 are made flush with a free face (top face in FIG. 10) of resin layer 9.

According to the modification method of FIGS. 9 and 10, resin layer 9 and light guide fiber bundle 6 can be formed as a combination, before the fiber bundle, lens frame, object lens, and sheath are assembled. Resin layer 9 can be polished safely and surely, without damaging other elements such as an object lens. Since resin layer 9 can be provided with a smooth free surface, stable light transmission is ensured. If a defect is found in resin layer 9, it is sufficient to dispose of light guide fiber bundle 6, without affecting other elements. Therefore, the structural elements of the endoscope can be efficiently used, and the total manufacturing cost can be reduced.

FIGS. 11 and 12 show the second modification of the method of manufacturing the resin layer.

In FIG. 11, mold 30 of PTFE has recess portion or annular groove 31 of a depth Δ1. The upper end of groove 31 is open to the outside. Resin 32 (as mentioned above) is filled in groove 31. As in the first modification, resin 32 is filled in groove 31 up to the same level as, or a little higher level than, the end face (top face in FIG. 11) of mold 30. After resin 32 is hardened, the end face (top face) of mold 30 is polished to smooth the free surface of resin 32. Hollow cylindrical resin layer 9, having a small axial length, is removed from mold 30. Then, as shown in FIG. 12, resin layer 9 is mounted on the end portion of insertion section 1 constituted in advance by sheath 2, lens frame 3, object lens group 4, an image guide fiber bundle, and light guide fiber bundle 6.

As in the first embodiment, insertion section 1 has at its end portion (top end in FIG. 12) annular groove 8 which has an outer peripheral wall defined by the inner wall of sheath 2, an inner peripheral wall defined by the outer wall of lens frame 3, and a bottom wall defined by end face 7 of light guide fiber bundle 6. The size of groove 8 corresponds to that of resin layer 9 formed by the method shown in FIG. 11. An adhesive for attaching resin layer 9 to groove 8 should be of the type similar to resin 32 or resin layer 9. (For example, when resin 32 is epoxy resin, the adhesive should be made of epoxy material.)

According to the above-mentioned method, there is no fear of damaging light guide fiber bundle 6, while polishing resin layer 9, and resin layer 9 can be economically manufactured.

Polytetrafluoroethylene (PTFE) is used as material of mold 20 of the first modification shown in FIG. 9, and mold 30 of the second modification shown in FIG. 11. However, other suitable resins can be employed.

An endoscope shown in FIGS. 13 and 14, which is an example relating to the present invention, will now be described.

This endoscope has a very thin insertion section which can be inserted into, for example, a blood vessel. While the small diameter of the insertion section is maintained, a damage to optical fibers within the insertion section can be prevented.

As shown in FIGS. 13 and 14, insertion section 1 has an outer diameter which is allowed to enter the blood vessel. Sheath 2 is made of resilient resin such as PTFE in a hollow cylindrical shape. The wall thickness of sheath 2 is small. Lens frame 3 is arranged at a center area of sheath 2 in the vicinity of an end portion (left portion in FIG. 13) of insertion section 1. Object lens group 4 having a cover glass and an object lens is secured within lens frame 3.

Image guide fiber bundle 5 has hard end portion 5a formed by connecting a number of optical fibers in a solid cylindrical shape by using an adhesive or synthetic resin. At least a part of hard end portion 5a is inserted into lens frame 3, and fixed at a predetermined position. The axial length of hard end portion 5a is determined such that, when hard end portion 5a is arranged at a predetermined position within lens frame 3, distance L1 is kept between plane C normal to the axis of insertion section 1 including rear end 15 and plane A normal to the axis of sheath 2 including its end face.

Light guide fiber bundle 6, which is arranged around lens frame 3 within sheath 2, is formed by bonding a number of optical fibers by an adhesive or synthetic resin. Fiber bundle 6 has hollow cylindrical hard end portion 6a into which lens frame 3 can be inserted. The axial length of hard end portion 6a is determined such that, when hard end portion 6a is arranged at a predetermined position within sheath 2, distance L2 is kept between plane D normal to the axis of insertion section 1 including rear end 16 and plane A normal to the axis of sheath 2 including its end face. The inner peripheral surface of hard end portion 6a is attached on lens frame 3, and the outer peripheral surface of hard end portion 6a is attached on sheath 2.

The lengths of image guide fiber bundle 5 and light guide fiber bundle 6 are determined such that, when they are assembled within sheath 2, the relationship in length between hard end portions 5a and 6a becomes L1≦L2. Accordingly, at the end portion of insertion section 1, the entire length of hard end portion 5a of image guide fiber bundle 5 is covered by hard end portion 6a of light guide fiber bundle 6.

Hard end portion 5a and hard rear edge 15 of image guide fiber bundle 5, which are protected by hard end portion 6a of light guide fiber bundle 6, are not damaged by external force due to shock or bending moment applied to the end portion of insertion section 1. While the outer diameter of insertion section 1 is limited to a small value, optical fibers of image guide fiber bundle 5 can be protected against external force, and high durability of the fibers is ensured.

FIGS. 15 and 16 show a second example relating to the present invention.

In this example, as in the second embodiment (FIGS. 4 and 5), forceps channel 11 is formed within insertion section 1.

In the second example, axially extending cylindrical spaces 13 and 14 are formed within hard end portion 6a of light guide fiber bundle 6, for containing lens frame 3 and tube 12 defining channel 11.

When fiber bundles 5 and 6 are assembled, the distance L1 between plane A including the end face of sheath 2 and plane C including rear edge 15 of hard end portion 5a is equal or smaller than the distance L2 between plane A and plane D including rear edge 16 of hard end portion 6a. Thus, end portion 5a, which is the weakest part of image guide fiber bundle 5, can be protected by hard end portion 6a of light guide fiber bundle 6.

As is obvious to one skilled in the art, the endoscopes of the examples of FIGS. 13-14 and FIGS. 15-16 may be provided with resin layers for sealing the inside of the sheaths, as mentioned above.

Various embodiments and modifications of the present invention have been described above. However, further modifications may be allowed within the scope of the claims of the invention.

What is claimed is:

1. An endoscope comprising:
   a small-diameter insertion section able to enter a body cavity, the insertion section having a hollow cylindrical member one end of which has an opening to the outside, said cylindrical member containing a light guide fiber bundle for emitting a beam of illumination light into the body cavity, an object optical system for receiving a beam reflected from the body cavity, to form an image, and image transmission means for transmitting the image formed;
   a recess portion having a side wall defined by said cylindrical member, a bottom wall defined by said light guide fiber bundle, and an opening at said one end of the cylindrical member; and a transparent resin layer of a uniform thickness, arranged within said recess portion and sealing the inside of said cylindrical member at said one end thereof, said resin layer having an end face which is substantially flush with said one end of the cylindrical member.

2. The endoscope according to claim 1, wherein said insertion section has an outer diameter such as to enable it to enter a blood vessel.

3. The endoscope according to claim 1, further comprising a lens frame arranged within said cylindrical member and exposed to the outside at said opening of said cylindrical member, said lens frame containing said object optical system and at least a portion of an image guide fiber bundle serving as said image transmission means, and having a free end substantially flush with said one end of the cylindrical member.

4. The endoscope according to claim 1, wherein said cylindrical member is formed of a multi-lumen tube.

5. The endoscope according to claim 1, further comprising a forceps channel extending within said insertion section and opening at said opening at said one end of the cylindrical member, said forceps channel having a free end substantially flush with said one end of the cylindrical member.

6. The endoscope according to claim 3, wherein said image guide fiber bundle and said light guide fiber bundle have hard end portions made hard by an adhesive or synthetic resin, and said hard end portions are arranged within said cylindrical member so that the length $L_1$ of the hard end portion of the image guide fiber bundle as measured from the end face of the cylindrical member is equal to or less than the length $L_2$ of the hard end portion of the light guide fiber bundle as measured from the end face of the cylindrical member.

7. The endoscope according to claim 5, wherein said resin layer is formed by filling said recess portion with a transparent adhesive and hardening the same.

8. The endoscope according to claim 3, wherein said resin layer is composed of a transparent adhesive and has dimensions corresponding to said recess portion and is hardened in advance integrally with said light guide fiber bundle, and the end portion of said resin layer has a smooth polished surface arranged to face said light guide fiber bundle.

9. The endoscope according to claim 3, wherein said resin layer is formed, in advance, of a hardened transparent adhesive and has dimensions corresponding to said recess portion, said resin layer being bonded to said cylindrical member, said light guide fiber bundle, and said lens frame within said recess portion, and having a smooth polished surface arranged to face said light guide fiber bundle.

10. The endoscope according to claim 3, wherein said adhesive is composed of epoxy resin.

11. The endoscope according to claim 5, wherein said adhesive is composed of epoxy resin.

* * * * *